(12) United States Patent
Barniak et al.

(10) Patent No.: US 11,944,638 B2
(45) Date of Patent: *Apr. 2, 2024

(54) OPHTHALMIC SOLUTIONS

(71) Applicant: Bausch + Lomb Ireland Limited, Dublin (IE)

(72) Inventors: Vicki Barniak, Fairport, NY (US); Catherine Scheuer, West Henrietta, NY (US); William T. Reindel, Webster, NY (US); John Michael Duex, Livonia, NY (US); Andrea E. Siverling, Rochester, NY (US)

(73) Assignee: Bausch + Lomb Ireland Limited (IE)

(*) Notice: Subject to any disclaimer, the term of this patent is extended or adjusted under 35 U.S.C. 154(b) by 0 days.

This patent is subject to a terminal disclaimer.

(21) Appl. No.: 17/691,265

(22) Filed: Mar. 10, 2022

(65) Prior Publication Data

US 2022/0288107 A1    Sep. 15, 2022

Related U.S. Application Data

(60) Provisional application No. 63/159,097, filed on Mar. 10, 2021.

(51) Int. Cl.

| | |
|---|---|
| *A61K 31/728* | (2006.01) |
| *A01N 33/12* | (2006.01) |
| *A01N 37/52* | (2006.01) |
| *A01P 1/00* | (2006.01) |
| *A61K 9/00* | (2006.01) |
| *A61K 47/02* | (2006.01) |
| *A61K 47/10* | (2017.01) |
| *A61K 47/26* | (2006.01) |
| *A61L 12/14* | (2006.01) |
| *A61P 27/04* | (2006.01) |
| *C11D 1/66* | (2006.01) |
| *C11D 1/722* | (2006.01) |
| *C11D 3/00* | (2006.01) |
| *C11D 3/04* | (2006.01) |
| *C11D 3/20* | (2006.01) |
| *C11D 3/22* | (2006.01) |
| *C11D 3/48* | (2006.01) |

(52) U.S. Cl.
CPC ............ *A61K 31/728* (2013.01); *A01N 33/12* (2013.01); *A01N 37/52* (2013.01); *A01P 1/00* (2021.08); *A61K 9/0048* (2013.01); *A61K 47/02* (2013.01); *A61K 47/10* (2013.01); *A61K 47/26* (2013.01); *A61L 12/142* (2013.01); *A61L 12/145* (2013.01); *A61P 27/04* (2018.01); *C11D 1/66* (2013.01); *C11D 1/722* (2013.01); *C11D 3/0078* (2013.01); *C11D 3/046* (2013.01); *C11D 3/2065* (2013.01); *C11D 3/222* (2013.01); *C11D 3/227* (2013.01); *C11D 3/48* (2013.01)

(58) Field of Classification Search
None
See application file for complete search history.

(56) References Cited

U.S. PATENT DOCUMENTS

| | | | |
|---|---|---|---|
| 4,758,595 | A | 7/1988 | Ogunbiyi et al. |
| 5,573,726 | A | 11/1996 | Dassanayake et al. |
| 6,180,093 | B1 | 1/2001 | De et al. |
| 6,517,933 | B1 | 2/2003 | Soane et al. |
| 8,119,112 | B2 | 2/2012 | Xia et al. |
| 8,759,321 | B2 | 6/2014 | Burke et al. |
| 9,096,819 | B2 | 8/2015 | Xia et al. |
| 9,309,357 | B2 | 4/2016 | Awasthi et al. |
| 2003/0044468 | A1 | 3/2003 | Cellesi et al. |
| 2014/0221309 | A1 | 8/2014 | Beard et al. |
| 2018/0098937 | A1 | 4/2018 | Horn |
| 2020/0000954 | A1 | 1/2020 | Awasthi et al. |

FOREIGN PATENT DOCUMENTS

| | | |
|---|---|---|
| EP | 0929292 B1 | 5/2001 |
| WO | 2018071619 A1 | 4/2018 |

OTHER PUBLICATIONS

Rinaudo, et al. "Effect of Mannitol on Hyaluronic Acid Stability in Two in Vitro Models of Oxidative Stress" Polymers, 1 (2014) 6, pp. 1948-1957.
International Search Report and Written Opinion of the International Searching Authority for PCT/EP2022/056158 dated Jun. 27, 2022, 12 pages.
Hartog et al., "Erythritol is a sweet antioxidant", Nutrition, 2010, vol. 26, Issue 4, pp. 449-458.
U.S. Appl. No. 17/691,260, filed Mar. 10, 2022.
U.S. Appl. No. 17/691,263, filed Mar. 10, 2022.

*Primary Examiner* — Dale R Miller
(74) *Attorney, Agent, or Firm* — Michael E. Carmen; John E. Thomas

(57) ABSTRACT

An ophthalmically compatible solution includes (a) about 0.005 to about 2 wt. %, based on the total weight of the ophthalmically compatible solution, of hyaluronic acid or a salt thereof; (b) about 0.01 to about 1 wt. %, based on the total weight of the ophthalmically compatible solution, of erythritol; (c) sodium chloride, potassium chloride or any combination thereof; and (d) one or more buffers.

21 Claims, No Drawings

OPHTHALMIC SOLUTIONS

PRIORITY CLAIM

The present application claims priority to U.S. Provisional Patent Application Ser. No. 63/159,097, entitled "Ophthalmic Solutions," filed Mar. 10, 2021, the content of which is incorporated by reference herein in its entirety.

BACKGROUND

During normal use, contact lenses become soiled or contaminated with a wide variety of compounds that can degrade lens performance. For example, a contact lens will become soiled with biological materials such as proteins or lipids that are present in the tear fluid and which adhere to the lens surface. Also, by handling of the contact lens, sebum (skin oil), cosmetics or other materials can soil the contact lens. These biological and external contaminants can affect visual acuity and patient comfort during use and at the end of the day. Accordingly, it is important to remove any debris from the lens surface for continued comfortable use with a lens care cleaning and disinfecting solution that contains one or more cleaning components. It can also be important that a lens care cleaning and disinfecting solution provide a contact lens consumer with some level of ocular comfort or hydration, particularly, consumers diagnosed with keratoconjunctivitis sicca, a condition often referred to as dry eye syndrome.

SUMMARY

In accordance with an illustrative embodiment, an ophthalmically compatible solution comprises (a) about 0.005 to about 2 wt. %, based on the total weight of the ophthalmically compatible solution, of hyaluronic acid or a salt thereof; (b) about 0.01 to about 1 wt. %, based on the total weight of the ophthalmically compatible solution, of erythritol; (c) sodium chloride, potassium chloride or any combination thereof; and (d) one or more buffers. The ophthalmically compatible solution may be administered to the eye that is not wearing a contact lens, e.g., to rewet the cornea.

In accordance with another illustrative embodiment, a method for reducing, ameliorating, treating, or controlling a condition of dry eye comprises administering to an affected eye of a patient an ophthalmically compatible solution comprising (a) about 0.005 to about 2 wt. %, based on the total weight of the ophthalmically compatible solution, of hyaluronic acid or a salt thereof; (b) about 0.01 to about 1 wt. %, based on the total weight of the ophthalmically compatible solution, of erythritol; (c) sodium chloride, potassium chloride or any combination thereof; and (d) one or more buffers.

In accordance with a further illustrative embodiment, a method of rewetting a cornea comprises administering an ophthalmically compatible solution to a cornea, the ophthalmically compatible solution comprising (a) about 0.005 to about 2 wt. %, based on the total weight of the ophthalmically compatible solution, of hyaluronic acid or a salt thereof; (b) about 0.01 to about 1 wt. %, based on the total weight of the ophthalmically compatible solution, of erythritol; (c) sodium chloride, potassium chloride or any combination thereof; and (d) one or more buffers.

In accordance with yet a further illustrative embodiment, a system useful as an artificial tear or for rewetting or lubricating a cornea is provided, the system comprising a drop dispenser capable of holding between about 1 and about 30 ml of an ophthalmically compatible solution comprising (a) about 0.005 to about 2 wt. %, based on the total weight of the ophthalmically compatible solution, of hyaluronic acid or a salt thereof; (b) about 0.01 to about 1 wt. %, based on the total weight of the ophthalmically compatible solution, of erythritol; (c) sodium chloride, potassium chloride or any combination thereof; and (d) one or more buffers.

In accordance with still yet a further illustrative embodiment, use of an ophthalmically compatible solution for rewetting a cornea, the ophthalmically compatible solution comprising (a) about 0.005 to about 2 wt. %, based on the total weight of the ophthalmically compatible solution, of hyaluronic acid or a salt thereof; (b) about 0.01 to about 1 wt. %, based on the total weight of the ophthalmically compatible solution, of erythritol; (c) sodium chloride, potassium chloride or any combination thereof; and (d) one or more buffers.

In accordance with still yet a further illustrative embodiment, use of an ophthalmically compatible solution for reducing, ameliorating, treating, or controlling a condition of dry eye of a patient, the ophthalmically compatible solution comprising (a) about 0.005 to about 2 wt. %, based on the total weight of the ophthalmically compatible solution, of hyaluronic acid or a salt thereof; (b) about 0.01 to about 1 wt. %, based on the total weight of the ophthalmically compatible solution, of erythritol; (c) sodium chloride, potassium chloride or any combination thereof; and (d) one or more buffers.

DETAILED DESCRIPTION

Various illustrative embodiments described herein include an ophthalmic solution such as an ophthalmically compatible solution useful, for example, as rewetting drops or eye drops that may be administered to the eye that is not wearing a contact lens, e.g., to rewet the cornea. Other illustrative embodiments described herein are also directed to ophthalmically compatible solutions useful, for example, in reducing, ameliorating, treating, or controlling a condition of dry eye.

Dry eye, also known generically as keratoconjunctivitis sicca and dyslacrima, is a common ophthalmological disorder affecting millions of people. A patient with dry eye may experience burning, a feeling of dryness and persistent irritation. In severe cases, dry eye can seriously impair a person's vision and hence handicap the sufferer in activities such as driving. Certain diseases such as Sjogren's disease manifest dry eye symptoms. Also, as people age, the lacrimal ducts in the eye may produce less moisture, resulting in eyes that become dry, inflamed, itchy and gritty.

Although it appears that dry eye may result from a variety of underlying, unrelated pathogenic causes, all presentations of the condition share a common effect, namely, the breakdown of the pre-ocular tear film, which commonly results in dehydration of the exposed outer surface of the eye and hence the symptoms described above.

A number of approaches exist for the treatment of dry eye. One common approach has been to supplement the ocular tear film with artificial tears throughout the day. Examples of the tear substitute approach include the use of buffered, isotonic saline solutions and aqueous solutions containing water-soluble polymers that render the solutions more viscous and thus less easily shed by the eye by the washing action of the tear fluid.

Soft contact lenses have been available since the 1980s. While there are many people who can successfully wear contact lenses, there are a number of people who can wear contact lenses for only short periods of time due to contact lens related dry eye. Symptoms of this disorder include thin and/or unstable tear films, corneal staining and subjective symptoms such as ocular discomfort, burning/stinging and dryness. Contact lens wear may trigger the onset of these symptoms or may exacerbate the symptoms. People with contact lens related dry eye generally can comfortably wear contact lenses only for limited periods of time (e.g., less than 6 hours and in some cases less than four hours).

Hyaluronic acid is a non-immunogenic substance and because of its viscoelastic and hydrophilic properties hyaluronic acid has been used for many years as an eye vitreous or joint fluid replacement or as a supportive medium in ophthalmic surgery. In joint fluids, the hyaluronic acid solution serves as a lubricant to provide a protective environment to the cells, and for this reason, it is used in the treatment of inflamed knee joints. The consumer use of products that include hyaluronic acid requires the manufacturer to sterilize the consumer product, and if used as an open multi-dose formulation, an additional step must be taken to preserve the formulation product.

Hyaluronic acid is one biopolymer known to be relatively sensitive to thermal sterilization processes. Heat sterilization of hyaluronic acid is known to accelerate the hydrolysis or oxidation of hyaluronic acid, thereby causing a significant and often detrimental decrease in the average molecular weight of the biopolymer. For many pharmaceutical applications, a relatively low molecular weight form of hyaluronic acid in the formulation is not desirable. Typically, the low molecular weight forms of hyaluronic acid do not provide the desired rheological properties of the high molecular weight form of hyaluronic acid. To compensate for the breakdown of the hyaluronic acid in the aforementioned heat sterilization methods, one could possibly begin with a hyaluronic acid with a higher molecular weight than desired. This accommodation, however, leads to process inefficiencies because the product yield of hyaluronic acid decreases as the average molecular weight of the biopolymer increases.

Illustrative embodiments described herein overcome the foregoing problems by formulating improved sterile, ophthalmically compatible aqueous solutions of hyaluronic acid or a salt thereof that can be subjected to sterilization without substantial degradation of the hyaluronic acid. In particular, by combining hyaluronic acid with erythritol in the ophthalmic solution disclosed herein, the molecular weight loss of hyaluronic acid over time when subjected to sterilization conditions such as autoclaving is statistically significantly better than an ophthalmic solution containing hyaluronic acid in the absence of erythritol. Thus, an ophthalmic solution disclosed herein in which the molecular weight loss of hyaluronic acid is improved will advantageously exhibit less pH issues, less efficacy issues, improved viscosity and less oxidative and thermal degradation thereby resulting in higher stability and longer shelf life. In addition, an ophthalmic solution disclosed herein also advantageously exhibits a higher tolerance to any iron contained in water used to prepare the solution, achieved by combining hyaluronic acid with erythritol and thereby providing a more robust solution.

In one or more non-limiting illustrative embodiments, an ophthalmic solution can be an ophthalmically compatible solution comprising (a) about 0.005 to about 2 wt. %, based on the total weight of the ophthalmically compatible solution, of hyaluronic acid or a salt thereof (b) about 0.01 to about 1 wt. %, based on the total weight of the ophthalmically compatible solution, of erythritol; (c) sodium chloride, potassium chloride or any combination thereof and (d) one or more buffers.

An ophthalmically compatible solution disclosed herein will include at least about 0.005 to about 2 wt. %, based on the total weight of the ophthalmically compatible solution, of hyaluronic acid or a salt thereof. Hyaluronic acid is a well-known, naturally occurring, water soluble biodegradable polymer composed of two alternatively linked sugars, D-glucuronic acid and N-acetylglucosamine, linked via alternating β-(1,4) and β-(1,3) glycosidic bonds. Hyaluronic acid is distinguished from the other glycosaminoglycans, as it is free from covalent links to protein and sulphonic groups. Hyaluronic acid is ubiquitous in animals, with the highest concentration found in soft connective tissue. It plays an important role for both mechanical and transport purposes in the body, e.g., it gives elasticity to the joints and rigidity to the vertebrate disks, and it is also an important component of the vitreous body of the eye.

The hyaluronic acid polymer is hydrophilic and highly viscous in aqueous solution at relatively low solute concentrations. It often occurs naturally as the sodium salt, sodium hyaluronate. Methods of preparing commercially available hyaluronan and salts thereof are well known. Hyaluronan can be purchased from, for example Seikagaku Company; Clear Solutions Biotech, Inc.; Pharmacia Inc.; Sigma Inc.; HTL Biotechnology; Contipro; Bloomage Biotechnology Corporation, and many other suppliers. Hyaluronic acid has repeating units of the structure represented by the following formula:

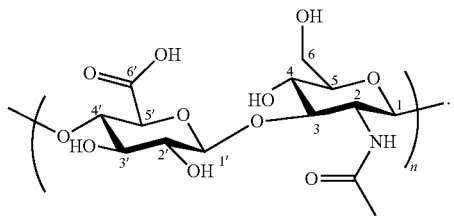

Accordingly, the repeating units in hyaluronic acid can be as follows:

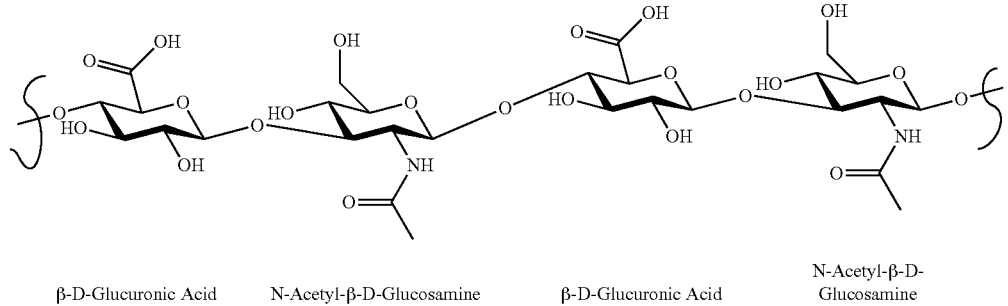

β-D-Glucuronic Acid     N-Acetyl-β-D-Glucosamine     β-D-Glucuronic Acid     N-Acetyl-β-D-Glucosamine In general, hyaluronic acid or a salt thereof such as sodium hyaluronate and potassium hyaluronate can have from about 2 to about 1,500,000 disaccharide units. In one embodiment, hyaluronic acid or a salt thereof can have a weight average molecular weight ranging from about 10,000 to about 3,000,000 Daltons (Da) in which the lower limit is from about 10,000, about 20,000, about 30,000, about 40,000, about 50,000, about 60,000, about 70,000, about 80,000, about 90,000, about 100,000, about 200,000, about 300,000, about 400,000, about 500,000, or about 600,000 Da, and the upper limit is about 200,000, about 300,000, about 400,000, about 500,000, about 600,000, about 700,000, about 800,000, about 900,000, about 1,000,000, or about up to 2,800,000 Da, where any of the lower limits can be combined with any of the upper limits.

In an illustrative embodiment, hyaluronic acid or a salt thereof is present in an ophthalmically compatible solution disclosed herein in an amount ranging from about 0.005 to about 2 wt. %, based on the total weight of the ophthalmically compatible solution. In another illustrative embodiment, hyaluronic acid or a salt thereof is present in an ophthalmically compatible solution disclosed herein in an amount ranging from about 0.01 to about 0.2 wt. %, based on the total weight of the ophthalmically compatible solution.

An ophthalmically compatible solution disclosed herein further contains erythritol. In an illustrative embodiment, erythritol is present in an ophthalmically compatible solution disclosed herein in an amount ranging from about 0.01 to about 1 wt. %, based on the total weight of the ophthalmically compatible solution. In another illustrative embodiment, erythritol is present in an ophthalmically compatible solution disclosed herein in an amount ranging from about 0.05 to about 0.5 wt. %, based on the total weight of the ophthalmically compatible solution. In another illustrative embodiment, erythritol is present in an ophthalmically compatible solution disclosed herein in an amount ranging from about 0.08 to about 0.4 wt. %, based on the total weight of the ophthalmically compatible solution.

The ophthalmically compatible solution disclosed herein further contains an effective amount of one or more tonicity adjusting components. Suitable tonicity adjusting components include, for example, those conventionally used in ophthalmic products such as various inorganic salts. In an illustrative embodiment, suitable tonicity adjusting components include sodium chloride, potassium chloride, and combinations thereof. The amount of the one or more tonicity adjusting components is an amount effective to provide the desired degree of tonicity to the solution.

In an illustrative embodiment, the one or more tonicity adjusting components are present in an ophthalmically compatible solution disclosed herein in an amount ranging from about 0.01 to about 5 wt. %, based on the total weight of the ophthalmically compatible solution. In another illustrative embodiment, the one or more tonicity adjusting components are present in an ophthalmically compatible solution disclosed herein in an amount ranging from about 0.01 to about 1 wt. %, based on the total weight of the ophthalmically compatible solution. In another illustrative embodiment, the one or more tonicity adjusting components are present in an ophthalmically compatible solution disclosed herein in an amount ranging from about 0.01 to about 0.08 wt. %, based on the total weight of the ophthalmically compatible solution.

The ophthalmically compatible solution disclosed herein further contains one or more buffers. The terms "buffer" and "buffer system" are understood to mean a compound that, alone or in combination with at least one other compound, provides a buffering system in solution that exhibits buffering capacity, that is, the capacity to neutralize, within limits, either acids or bases (alkali) with relatively little or no change in the original pH. The term "buffering capacity" is understood to mean the millimoles (mM) of a strong acid or base (or respectively, hydrogen or hydroxide ions) required to change the pH by one unit when added to one liter (a standard unit) of the buffer solution. The buffer capacity will depend on the type and concentration of the buffer components. The buffer capacity is measured from a starting pH of about 6 to about 8, or from about 7.4 to about 8.4.

Suitable buffers include, for example, boric acid and its salts such as sodium borate or potassium borate. Borate buffers also include buffer compounds such as, for example, potassium tetraborate or potassium metaborate that produce borate acid or its salt in solutions. Borate buffers are known for enhancing the efficacy of certain polymeric biguanides. For example, U.S. Pat. No. 4,758,595 describes a contact-lens solution containing poly(hexamethylene biguanide), also referred to as PHMB or PAPB, that can exhibit enhanced efficacy if combined with a borate buffer. Other suitable buffers include diglycine (glycylglycine) and sodium citrate.

In an illustrative embodiment, the one or more buffers are present in an ophthalmically compatible solution disclosed herein in an amount ranging from about 0.1 to about 10% (w/w). In another illustrative embodiment, the one or more buffers are present in an ophthalmically compatible solution disclosed herein in an amount ranging from about 0.5 to about 5% (w/w). In another illustrative embodiment, the one or more buffers are present in an ophthalmically compatible solution disclosed herein in an amount ranging from about 0.75 to about 2% (w/w).

An ophthalmically compatible solution disclosed herein can further contain an effective amount of one or more lubricant components. Suitable lubricant components include, for example, those conventionally used in ophthalmic products. In an illustrative embodiment, suitable lubricant components include nonionic diols, such as glycerol and propylene glycol and combinations thereof.

In an illustrative embodiment, the one or more lubricant components are present in an ophthalmically compatible solution disclosed herein in an amount ranging from about 0.01 to about 5 wt. %, based on the total weight of the ophthalmically compatible solution. In another illustrative embodiment, the one or more lubricant components are present in an ophthalmically compatible solution disclosed herein in an amount ranging from about 0.01 to about 1 wt. %, based on the total weight of the ophthalmically compatible solution.

An ophthalmically compatible solution disclosed herein may further contain, in addition to the foregoing components, one or more preservatives, comfort agents, pH adjusting agents, chelating agents, viscosity modifying agents, demulcents and the like. For example, the ophthalmically compatible solution disclosed herein may further contain one or more comfort or cushioning components. The comfort component can condition the lens surface rendering it more hydrophilic (less lipophilic) and/or to act as a demulcent on the eye. The comfort component is believed to cushion the impact on the eye surface during placement of the lens and serves also to alleviate eye irritation.

Suitable comfort components include, for example, water soluble natural gums, cellulose-derived polymers and the like. Useful natural gums include guar gum, gum tragacanth and the like. Useful cellulose-derived comfort components include cellulose-derived polymers, such as hydroxypropyl cellulose, hydroxypropylmethyl cellulose, carboxymethyl cellulose, methyl cellulose, hydroxyethyl cellulose and the like. Some non-cellulose comfort components include propylene glycol or glycerin. The comfort components can be present in the solution in an amount ranging from about 0.01% to about 1% (w/w).

In an illustrative embodiment, a comfort agent that is believed to maintain a hydrated corneal surface is polyvinylpyrrolidone (PVP). PVP is a linear homopolymer or essentially a linear homopolymer comprising at least 90% repeat units derived from 1-vinyl-2-pyrrolidone monomer, the remainder of the monomer composition can include neutral monomer, e.g., vinyl or acrylates. Other synonyms for PVP include povidone, polyvidone, 1-vinyl-2-pyrrolidinone, and 1-ethenyl-2-pyrolionone (CAS registry number 9003-39-8). PVP can have a weight average molecular weight from about 10,000 to about 250,000 or from about 30,000 to about 100,000. Such materials are sold by various companies, including ISP Technologies, Inc. under the trademark PLASDONE® K-29/32, from BASF under the trademark KOLLIDON®, for example, KOLLIDON® K-30 or K-90. It is also preferred that one use pharmaceutical grade PVP.

In an illustrative embodiment, an ophthalmically compatible solution disclosed herein does not contain a surfactant. In an illustrative embodiment, an ophthalmically compatible solution disclosed herein does not contain a nonionic surfactant. In an illustrative embodiment, an ophthalmically compatible solution disclosed herein does not contain one or more of a poloxamer and a poloxamine.

The ophthalmically compatible solutions disclosed herein are physiologically compatible. Specifically, the solutions must be "ophthalmically safe", that is, the solution is safe and comfortable for daily contact with the eye. An ophthalmically safe solution has a tonicity and pH that is compatible with the eye and comprises materials, and amounts thereof, that are non-cytotoxic according to ISO (International Standards Organization) standards and U.S. FDA regulations. The solutions should be sterile in that the absence of microbial contaminants in the product prior to release must be statistically demonstrated to the degree necessary for such products.

In non-limiting illustrative embodiments, the ophthalmically compatible solution disclosed herein can have an osmolality in the range of at least about 200 mOsmol/kg and up to about 400 mOsmol/kg, or from about 250 and up to about 400 mOsmol/kg. In illustrative embodiments, the ophthalmically compatible solution disclosed herein can have an osmolality in the range of at least about 200 mOsmol/kg and up to about 300 mOsmol/kg, or from about 250 and up to about 300 mOsmol/kg. The ophthalmically compatible solutions are substantially isotonic or hypertonic (for example, slightly hypertonic) and are ophthalmically acceptable.

In non-limiting illustrative embodiments, the ophthalmically compatible solution disclosed herein can have a pH within the range of pH of about 4.0 to about 9.0, or about 5.0 to about 8.0, or about 6.0 to about 8.0, or about 6.5 to about 7.8.

In illustrative embodiments, the ophthalmically compatible solution disclosed herein may be administered to the eye that is not wearing a contact lens, e.g., to rewet the cornea. In illustrative embodiments, the ophthalmically compatible solution disclosed herein may be formulated as an eye drop to soothe eye irritation. Examples of eye drops would be topical artificial tears and lubricants for dry eye which can be available Over-The-Counter (OTC) without prescription. These tear substitutes increase humidity at the ocular surface and to improve lubrication. In addition, artificial tears smooth the corneal surface of dry eye patients, an effect that contributes to improved vision.

In an illustrative embodiment, a method for reducing, ameliorating, treating, or controlling a condition of dry eye is provided. In an illustrative embodiment, the method comprises administering to an affected eye of a patient the ophthalmically compatible solution disclosed herein.

In accordance with a further illustrative embodiment, a method of rewetting a cornea is provided. In an illustrative embodiment, the method comprises administering an ophthalmically compatible rewetting solution disclosed herein.

In non-limiting illustrative embodiments, a system useful as an artificial tear or for rewetting or lubricating a cornea comprises a drop dispenser capable of holding between about 1 and about 30 ml of an ophthalmically compatible solution disclosed herein.

The following examples are provided to enable one skilled in the art to practice the invention and are merely illustrative. The examples should not be read as limiting the scope of the invention as defined in the claims.

Example 1

Preparation of an ophthalmically compatible solution suitable for rewetting a cornea. Amounts are wt % or ppm based on total weight of the solution with purified water used for q.s. to 100 wt. %.

A first solution was prepared by adding boric acid (0.6 wt. %), sodium borate (0.25 wt. %), potassium chloride (0.21 wt. %), erythritol (0.3 wt. %) and glycerol (0.5 wt. %). Samples of the solution were then heated to 40° C. or 75° C.

After cooling to room temperature, sodium hyaluronate (0.15 wt. %) was added and stirred overnight.

Various features of the ophthalmically compatible solutions disclosed herein are, for brevity, described in the context of a single embodiment, but may also be provided separately or in any suitable sub-combination. All combinations of the embodiments are specifically embraced by the illustrative embodiments disclosed herein just as if each and every combination was individually and explicitly disclosed. In addition, all sub-combinations listed in the embodiments describing such variables are also specifically embraced by the present compositions and are disclosed herein just as if each and every such sub-combination was individually and explicitly disclosed herein.

It will be understood that various modifications may be made to the embodiments disclosed herein. Therefore, the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the features and advantages appended hereto.

What is claimed is:

1. An ophthalmically compatible solution, consisting of:
   (a) about 0.005 to about 2 wt. %, based on the total weight of the ophthalmically compatible solution, of hyaluronic acid or a salt thereof;
   (b) about 0.01 to about 1 wt. %, based on the total weight of the ophthalmically compatible solution, of erythritol;

(c) sodium chloride, potassium chloride or any combination thereof;
(d) one or more buffers;
(e) glycerol; and
(f) water;
wherein the ophthalmically compatible solution is preservative-free.

2. The ophthalmically compatible solution of claim 1, consisting of:
about 0.01 to about 0.2 wt. %, based on the total weight of the ophthalmically compatible solution, of hyaluronic acid or a salt thereof; and
about 0.05 to about 0.5 wt. %, based on the total weight of the ophthalmically compatible solution, of erythritol.

3. The ophthalmically compatible solution of claim 1, consisting of:
about 0.01 to about 5 wt. %, based on the total weight of the ophthalmically compatible solution, of the sodium chloride, potassium chloride or any combination thereof; and
about 0.1 to about 10% (w/w) of the one or more buffers.

4. The ophthalmically compatible solution of claim 1, wherein the one or more buffers comprise boric acid or a salt thereof.

5. The ophthalmically compatible solution of claim 1, consisting of:
about 0.01 to about 0.2 wt. %, based on the total weight of the ophthalmically compatible solution, of hyaluronic acid or a salt thereof;
about 0.05 to about 0.5 wt. %, based on the total weight of the ophthalmically compatible solution, of erythritol;
about 0.01 to about 1 wt. %, based on the total weight of the ophthalmically compatible solution, of the sodium chloride, potassium chloride or any combination thereof; and
about 0.01 to about 5 wt. %, based on the total weight of the ophthalmically compatible solution, of glycerol.

6. The ophthalmically compatible solution of claim 1, in the form of eye drops.

7. A method for reducing, ameliorating, treating, or controlling a condition of dry eye, the method consisting of:
administering to an affected eye of a patient an ophthalmically compatible solution consisting of (a) about 0.005 to about 2 wt. %, based on the total weight of the ophthalmically compatible solution, of hyaluronic acid or a salt thereof; (b) about 0.01 to about 1 wt. %, based on the total weight of the ophthalmically compatible solution, of erythritol; (c) sodium chloride, potassium chloride or any combination thereof; (d) one or more buffers; and (e) glycerol; and (f) water;
wherein the ophthalmically compatible solution is preservative-free.

8. The method of claim 7, wherein the ophthalmically compatible solution consists of:
about 0.01 to about 0.2 wt. %, based on the total weight of the ophthalmically compatible solution, of hyaluronic acid or a salt thereof;
about 0.08 to about 0.4 wt. %, based on the total weight of the ophthalmically compatible solution, of erythritol;
about 0.01 to about 0.08 wt. %, based on the total weight of the ophthalmically compatible solution, of the sodium chloride, potassium chloride or any combination thereof; and
about 0.01 to about 5 wt. %, based on the total weight of the ophthalmically compatible solution, of glycerol.

9. The method of claim 7, wherein the ophthalmically compatible solution is in the form of eye drops.

10. A method of rewetting a cornea, the method consisting of:
administering an ophthalmically compatible solution to a cornea, wherein the ophthalmically compatible solution consists of (a) about 0.005 to about 2 wt. %, based on the total weight of the ophthalmically compatible solution, of hyaluronic acid or a salt thereof; (b) about 0.01 to about 1 wt. %, based on the total weight of the ophthalmically compatible solution, of erythritol; (c) sodium chloride, potassium chloride or any combination thereof; (d) one or more buffers; (e) glycerol; and (f) water;
wherein the ophthalmically compatible solution is preservative-free.

11. The method of claim 10, wherein the ophthalmically compatible solution consists of:
about 0.01 to about 0.2 wt. %, based on the total weight of the ophthalmically compatible solution, of hyaluronic acid or a salt thereof;
about 0.08 to about 0.4 wt. %, based on the total weight of the ophthalmically compatible solution, of erythritol;
about 0.01 to about 0.08 wt. %, based on the total weight of the ophthalmically compatible solution, of the sodium chloride, potassium chloride or any combination thereof; and
about 0.01 to about 5 wt. %, based on the total weight of the ophthalmically compatible solution, of glycerol.

12. The method of claim 10, wherein the ophthalmically compatible solution is in the form of eye drops.

13. A system useful as an artificial tear or for rewetting or lubricating a cornea, the system comprising a drop dispenser capable of holding between about 1 and about 30 ml of the ophthalmically compatible solution of claim 1.

14. An ophthalmically compatible solution, consisting of:
(a) about 0.005 to about 2 wt. %, based on the total weight of the ophthalmically compatible solution, of hyaluronic acid or a salt thereof;
(b) about 0.01 to about 1 wt. %, based on the total weight of the ophthalmically compatible solution, of erythritol;
(c) sodium chloride, potassium chloride or any combination thereof;
(d) one or more buffers;
(e) about 0.01 to about 5 wt. %, based on the total weight of the ophthalmically compatible solution, of glycerol; and
(f) water;
wherein the ophthalmically compatible solution is preservative-free.

15. The ophthalmically compatible solution of claim 14, wherein the one or more buffers are selected from the group consisting of boric acid and a salt of boric acid.

16. The ophthalmically compatible solution of claim 14, in the form of eye drops.

17. The ophthalmically compatible solution of claim 14, consisting of:
about 0.01 to about 0.2 wt. %, based on the total weight of the ophthalmically compatible solution, of hyaluronic acid or a salt thereof;
about 0.08 to about 0.4 wt. %, based on the total weight of the ophthalmically compatible solution, of erythritol;
about 0.01 to about 0.08 wt. %, based on the total weight of the ophthalmically compatible solution, of the sodium chloride, potassium chloride or any combination thereof; and
about 0.01 to about 1 wt. %, based on the total weight of the ophthalmically compatible solution, of glycerol.

18. The ophthalmically compatible solution of claim 14, wherein the hyaluronic acid or a salt thereof is sodium hyaluronate.

19. The system according to claim 13, wherein the ophthalmically compatible solution consists of:
- about 0.01 to about 0.2 wt. %, based on the total weight of the ophthalmically compatible solution, of hyaluronic acid or a salt thereof;
- about 0.05 to about 0.5 wt. %, based on the total weight of the ophthalmically compatible solution, of erythritol;
- about 0.01 to about 1 wt. %, based on the total weight of the ophthalmically compatible solution, of the sodium chloride, potassium chloride or any combination thereof; and
- about 0.01 to about 5 wt. %, based on the total weight of the ophthalmically compatible solution, of glycerol.

20. The system according to claim 13, wherein the one or more buffers are selected from the group consisting of boric acid and a salt of boric acid.

21. The system according to claim 13, wherein the ophthalmically compatible solution is in the form of eye drops.

\* \* \* \* \*